(12) United States Patent
Botzem et al.

(10) Patent No.: US 10,039,711 B2
(45) Date of Patent: Aug. 7, 2018

(54) SELF-ADHESIVE FILM FOR TEETH

(75) Inventors: Petra Botzem, Andernach (DE); Wolfgang Laux, Diez (DE)

(73) Assignee: LTS Lohmann Therapie-Systeme AG, Andernach (DE)

( * ) Notice: Subject to any disclaimer, the term of this patent is extended or adjusted under 35 U.S.C. 154(b) by 1150 days.

(21) Appl. No.: 11/664,949

(22) PCT Filed: Oct. 6, 2005

(86) PCT No.: PCT/EP2005/010749
§ 371 (c)(1),
(2), (4) Date: Apr. 9, 2007

(87) PCT Pub. No.: WO2006/040059
PCT Pub. Date: Apr. 20, 2006

(65) Prior Publication Data
US 2008/0286317 A1    Nov. 20, 2008

(30) Foreign Application Priority Data
Oct. 13, 2004    (DE) .......................... 10 2004 049 740

(51) Int. Cl.
| | | |
|---|---|---|
| A61Q 11/00 | (2006.01) | |
| A61K 8/02 | (2006.01) | |
| A61K 8/81 | (2006.01) | |
| A61K 9/00 | (2006.01) | |
| A61K 9/70 | (2006.01) | |

(52) U.S. Cl.
CPC ............ *A61K 9/006* (2013.01); *A61K 8/0208* (2013.01); *A61Q 11/00* (2013.01); *A61K 9/7007* (2013.01)

(58) Field of Classification Search
CPC ...... A61K 8/0208; A61K 9/006; A61K 9/007; A61Q 11/00
USPC .................................................. 424/49, 435
See application file for complete search history.

(56) References Cited

U.S. PATENT DOCUMENTS

| | | | | |
|---|---|---|---|---|
| 3,519,587 A | * | 7/1970 | Wiest et al. ................... | 524/564 |
| 4,772,470 A | * | 9/1988 | Inoue et al. ................... | 424/435 |
| 5,173,317 A | * | 12/1992 | Hartman et al. ................. | 426/6 |
| 5,747,017 A | | 5/1998 | Nichols et al. | |
| 6,582,708 B1 | * | 6/2003 | Sagel et al. ................... | 424/401 |
| 6,946,142 B2 | * | 9/2005 | Chang et al. ................. | 424/435 |
| 2004/0062724 A1 | * | 4/2004 | Moro et al. .................... | 424/53 |
| 2004/0077498 A1 | | 4/2004 | Lynch | |

FOREIGN PATENT DOCUMENTS

| | | | | |
|---|---|---|---|---|
| DE | 3407279 | | 8/1985 | |
| GB | 785119 | * | 10/1957 | |
| JP | 11240816 | | 9/1999 | |
| KR | 2003059552 | | 7/2003 | |
| WO | WO03/000216 | | 1/2003 | |
| WO | WO 2005/110344 A1 | * | 5/2004 | ............... A61K 7/16 |
| WO | WO05/110344 | | 11/2005 | |

OTHER PUBLICATIONS http://web.archive.org/web/20040311033617/http://www.medicinenet.com/script/main/art.asp?articlekey=10736, Water soluble vitamins vs fat soluble vitamins, Doctor's Answer, Mar. 10, 2004.*
Fatty Acids, http://www.cyberlipid.org/fa/acid0001.htm, pp. 1-21, Retrieved Sep. 30, 2017.*

* cited by examiner

*Primary Examiner* — Lezah Roberts
(74) *Attorney, Agent, or Firm* — ProPat, L.L.C.

(57) ABSTRACT

Monolayered or multilayered, film-shaped, pressure-sensitive adhesive preparations for application in the oral region and a process for manufacturing such preparations. The preparations contain at least one polymethyl vinyl ether-maleic acid anhydride copolymer, polyvinyl acetate and/or at least one copolymer of the polyvinyl acetate with vinyl alcohol esters of fatty acids, as well as at least one cosmetic and/or pharmaceutical active substance.

11 Claims, No Drawings

SELF-ADHESIVE FILM FOR TEETH

CROSS-REFERENCE TO RELATED APPLICATIONS

This application is a National Stage application of International Application No. PCT/EP2005/010749, filed on Oct. 6, 2005, which claims priority of German application number 10 2004 049 740.0, filed on Oct. 13, 2004.

BACKGROUND OF THE INVENTION

Field of the Invention

The present invention relates to film-shaped preparations which are pressure-sensitive adhesive to teeth, gums or the oral mucosa and which are suitable for cosmetic or medical treatment of the teeth, especially the tooth necks, and of the gums. In addition, the present invention relates to a process for manufacturing such film-shaped preparations.

Description of the Prior Art

Products for cleaning one's mouth and for active substance delivery having the form of pastes, creams or mouth rinses have long since been known and have been available on the market. These products include tooth pastes and creams which have a cleaning effect, protect against caries, are desensitizing, or have a bleaching effect. Also known are creams, gels and ointments that are applied in the oral region for treating local illnesses and disorders such as anti-inflammatory remedies, analgesic remedies and/or tonics.

For some years, film-shaped, flat-shaped or strip-shaped oral application forms have also been commercially available and are used for cosmetic or therapeutic purposes. These application forms include, for example, the Listerine POCKET-PAKS ® by Pfizer or the "Teeth Whitestrips" by Procter & Gamble. Such application forms are as a rule based on films made up of water-soluble polymers which disintegrate rather quickly on use and are therefore not suitable for a longer-lasting treatment.

In addition, products are known that consist of several layers, such as those disclosed in U.S. Pat. No. 6,582,708, which, however, include only one flexible layer and which, due to their overall thickness of up to 3 mm, are disturbing and unpleasant in the mouth.

The recipes and methods used in manufacturing the known film-shaped application forms, for the most part, start from water or from water-containing alcoholic polymer solutions. A disadvantage here is that there are limitations to preparing a completely dissolved formulation of lipophile, poorly water-soluble active substances or of active substances that are sensitive to water.

SUMMARY OF THE PRESENT INVENTION

The object of the present invention was thus to provide a mono-layered or multilayered, water-soluble or at least partially water-swellable, film-shaped material which has good adhesion to teeth, gums or the oral mucosa, which is suitable as an active substance carrier, and which does not begin to disintegrate within a few seconds. More particularly, the object is to provide a film-shaped material of the afore-mentioned type which enables administration of water-insoluble or water-sensitive active substances.

This object is achieved by providing a mono-layered or multilayered, pressure-sensitive-adhesive, film-shaped preparation which contains at least one polymethyl vinyl ether-maleic acid anhydride copolymer, polyvinyl acetate and/or at least one copolymer of the vinyl acetate with vinyl alcohol esters of fatty acids, as well as at least one cosmetic and/or pharmaceutically active substance.

DETAILED DESCRIPTION OF THE PRESENT INVENTION

Preferably, the content of polymethyl vinyl ether-maleic acid anhydride copolymer in the film-shaped, pressure sensitive adhesive preparations is 5 to 35%-wt.

The content of polyvinyl acetate and/or of the copolymer (s) of the vinyl acetate with vinyl alcohol esters of fatty acids in the film-shaped, pressure-sensitive-adhesive preparations preferably amounts to 4 to 35%-wt. The film-shaped, pressure-sensitive adhesive preparations in addition have a content of at least one cosmetic and/or pharmaceutical active substance which is determined by the nature of the illness or by the cosmetic needs. The active substance is preferably a poorly water-soluble active substance or a water-sensitive active substance.

It should be appreciated that the term "poorly water-soluble active substances" means such active substances which have a solubility in water of less than 1 g/l. These include, for example, griseofulvin, estradiol and vitamin $D_3$.

The water-sensitive active substances include active substances of which the aqueous solution loses more than 0.1% of its active substance content within 24 hours at room temperature due to decomposition of the active substance. The water-sensitive active substances include, for example, acetylsalicylic acid and iodine.

In a particularly preferred embodiment, the film-shaped, pressure-sensitive adhesive preparation also contains carboxymethyl cellulose and/or one of its salts. The content of carboxymethyl cellulose or of one of its salts in the preparation amounts to 5 to 35%-wt.

To manufacture the film-shaped preparations, which are pressure-sensitive adhesive on teeth, gums or the oral mucosa, the various, water-soluble and/or water-swellable polymers are mixed with at least one active substance in solutions containing organic solvents as the main component. This mixture is used to coat a substrate, and the coated substrate is dried, optionally by application of heat.

The advantages of the invention arise especially where mixtures of polymethyl vinyl ether-maleic acid anhydride copolymers with polyvinyl acetate or the copolymers of the vinyl acetate with vinyl alcohol esters of fatty acids are used.

The content of polymethyl vinyl ether-maleic acid anhydride copolymer is preferably 5 to 35%-wt., and the content of polyvinyl acetate and/or the copolymer(s) of the vinyl acetate with vinyl alcohol esters of fatty acids is preferably 4 to 35%-wt., in each case relative to the solids content.

The polymethyl vinyl ether-maleic acid anhydride copolymers sold under the name of "GANTREZ®" by the firm of ISP, and the polyvinyl acetates or copolymers of the vinyl acetate with vinyl alcohol esters of fatty acids, designated as "VINNAPAS®", of the firm of Wacker Polymer Systems, Burghausen, have proved to be particularly suitable in accordance with the present invention.

Any solvents which dissolve the polymethyl vinyl ether-maleic acid anhydride copolymers and polyvinyl acetate or copolymers of the vinyl acetate with vinyl alcohol esters of fatty acids may be used as the organic solvents which, in the method according to the invention, are contained in the solution as the main component thereof. Of these organic solvents, those which are preferably used are ones which also mix with water since by adding small amounts of water, e.g. of 1 to 5%-wt., the dissolving power for the polymers and the active substance/active substances can be adapted to the given requirements. Particular preference is given to those organic solvents which permit addition of the active substance dissolved in ethanol or in an ethanol-water mixture. The especially preferred organic solvent is selected from the group consisting of methyl ethyl ketone, ethyl acetate, ethanol, acetone and mixtures thereof.

The consistency and/or tackiness of the resultant film-shaped preparations can be adapted to the demands placed on the product by altering the mixing ratio of ethanol and methyl ethyl ketone. Solvent mixtures containing an ethanol portion of 5 to 20%-wt., relative to the total solvent, have proved advantageous.

To manufacture a preferred embodiment enabling a particularly successful adhesion of the film-shaped preparations on the teeth, gums and/or oral mucosa, carboxymethyl cellulose and/or at least one of its salts is added to the polymer mixture.

Preferably, 5 to 35%-wt. of carboxymethyl cellulose or at least one of its salts, relative to the solids content, is added to the polymer mixture.

To manufacture the preparation according to the invention, at least one polymethyl vinyl ether-maleic acid anhydride copolymer and polyvinyl acetate and/or at least one copolymer of the vinyl acetate with vinyl alcohol esters of fatty acids, together with at least one active substance and, optionally, carboxymethyl cellulose and/or at least one of its salts, are mixed in a solution containing one or several organic solvents as the main component of the solution. The resultant compound is applied in liquid form to a support and freed from the solvent mixture, so that a film having a layer thickness of 4 to 2000 μm, preferably 40 to 500 μm, and particularly preferably 60 to 250 μm, is obtained.

Multilayer, pressure-sensitive-adhesive film-shaped preparations, with which it is possible to achieve, for example, an improved adhesion of the preparation to teeth, can be prepared, for example, by hot lamination, by coating already existent layers with further solvent-containing compounds, as described hereinabove in connection with the manufacture of a monolayer film, or by other processes known to those skilled in the art.

Pieces having a size appropriate to the respective given purposes are then punched out from the film or laminate.

The process according to the present invention results in film-shaped preparations which adhere to teeth, gums or the oral mucosa, which do not begin to disintegrate within a few seconds, and by which water-insoluble and even water-sensitive active substances can be administered. These preparations may advantageously be utilised for medical or cosmetic treatments.

EXAMPLE 5 g of a 33.3% solution (%-wt.) of a vinyl acetate-based polymer in methyl ethyl ketone and 3 g of a 15% solution (%-wt.) of polymethyl vinyl ether-maleic acid anhydride (=copolymer of methyl vinyl ether and maleic acid anhydride) in ethyl acetate were added together and homogenised. This resulted in a solution which was spread at various coating thicknesses and, subsequently, dried. This yielded flexible films which adhered both to the oral mucosa and to the teeth.

What has been described above are preferred aspects of the present invention. It is of course not possible to describe every conceivable combination of components or methodologies for purposes of describing the present invention, but one of ordinary skill in the art will recognize that many further combinations and permutations of the present invention are possible. Accordingly, the present invention is intended to embrace all such alterations, combinations, modifications, and variations that fall within the spirit and scope of the appended claims.

The invention claimed is:

1. An at least one layer, pressure-sensitive-adhesive preparation in the form of a film for application in the oral region, said preparation comprising:
   (i) a layer of pressure sensitive adhesive consisting essentially of at least a polymethyl vinyl ether-maleic acid anhydride copolymer, wherein the content of polymethyl vinyl ether-maleic acid anhydride copolymer is 5 to 35%-wt.;
   at least a copolymer of vinyl acetate with vinyl alcohol esters of lauric acid, wherein the content of the copolymer of the vinyl acetate with vinyl alcohol esters of lauric acid amounts to 4 to 35%-wt.;
   optional carboxymethyl cellulose, and/or at least one salt of said carboxymethyl cellulose,
   and (ii) at least one cosmetic active substance and/or pharmaceutical active substance, wherein said preparation has a layer thickness of 4 to 2000 μm,
   said pressure-sensitive-adhesive preparation adheres to teeth, gums or oral mucosa and does not disintegrate within a few seconds.

2. The preparation according to claim 1, wherein the active substance is poorly soluble in water or is sensitive to water.

3. The preparation according to claim 1, further comprising an additional content of carboxymethyl cellulose and/or at least one salt of said carboxymethyl cellulose.

4. The preparation according to claim 3, wherein the content of carboxymethyl cellulose and/or the salt of said carboxymethyl cellulose is 5 to 35%-wt.

5. The preparation according to claim 1, wherein said preparation has a layer thickness 40 to 500 μm.

6. The preparation according to claim 5, wherein said preparation has a layer thickness of 60 to 250 μm.

7. The preparation according to claim 1, wherein said film is prepared from a solution containing ethanol and methyl ethyl ketone as a solvent mixture, and wherein said mixture comprises an ethanol portion of 5-20%-wt. relative to the total solvent mixture, to adapt the consistency and/or tackiness of the resulting preparation.

8. An at least one layer, pressure-sensitive-adhesive preparation in the form of a film for application in the oral region, said preparation comprising at least one cosmetic active substance and/or pharmaceutical active substance and
   a layer of pressure-sensitive-adhesive consisting of a polymethyl vinyl ether-maleic acid anhydride copolymer, wherein the content of polymethyl vinyl ether-maleic acid anhydride copolymer is 5 to 35%-wt.;
   at least a copolymer of vinyl acetate with vinyl alcohol esters of lauric acid, wherein the content of the copolymer of the vinyl acetate with vinyl alcohol esters of lauric acid amounts to 4 to 35%-wt.;
   and optional carboxymethyl cellulose and/or at least one salt of said carboxymethyl cellulose,
   wherein said polymethyl vinyl ether-maleic acid anhydride copolymer and said copolymer of vinyl acetate are present in a ratio of 1:3.7.

9. The preparation according to claim 1, wherein the film is formed from a homogenized solution.

10. The preparation according to claim 1, wherein the pressure-sensitive-adhesive consists of water-soluble and/or water-swellable polymers.

11. The preparation according to claim 3, wherein said film is mono-layered.

\* \* \* \* \*